(12) United States Patent
Chang (10) Patent No.: US 8,668,676 B2
(45) Date of Patent: Mar. 11, 2014

(54) APPARATUS AND METHODS FOR IMPLANTING PARTICULATE OCULAR IMPLANTS

(75) Inventor: James N. Chang, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 755 days.

(21) Appl. No.: 12/495,314

(22) Filed: Jun. 30, 2009

(65) Prior Publication Data

US 2009/0264813 A1 Oct. 22, 2009

Related U.S. Application Data

(63) Continuation-in-part of application No. 11/455,392, filed on Jun. 19, 2006, now abandoned.

(51) Int. Cl.
| | |
|---|---|
| *A61M 5/32* | (2006.01) |
| *A61F 9/00* | (2006.01) |
| *A61M 31/00* | (2006.01) |
| *A61K 9/22* | (2006.01) |

(52) U.S. Cl.
USPC .......... 604/274; 604/501; 604/891.1; 604/61; 606/67

(58) Field of Classification Search
USPC .................. 604/274, 501, 891.1, 61; 606/107
See application file for complete search history.

(56) References Cited

U.S. PATENT DOCUMENTS

| | | | |
|---|---|---|---|
| 2,513,014 A | 6/1950 | Fields | |
| 2,717,599 A * | 9/1955 | Huber | 604/274 |
| 3,220,413 A | 11/1965 | Sunnen | |
| 3,238,941 A | 3/1966 | Klein et al. | |
| 3,698,390 A | 10/1972 | Ferris | |
| 3,937,370 A | 2/1976 | Witty | |
| 4,105,030 A * | 8/1978 | Kercso | 604/506 |
| 4,144,317 A | 3/1979 | Higuchi et al. | |

(Continued)

FOREIGN PATENT DOCUMENTS

| | | |
|---|---|---|
| EP | 0197718 | 10/1986 |
| EP | 0270257 | 6/1988 |

(Continued)

OTHER PUBLICATIONS

Gilman, A.G., et al., eds. (1990). Goodman and Gilman's: The Pharmacological Basis of Therapeutics. 8$^{th}$ Edition, Pergamon Press: New York, p. 1447.

(Continued)

*Primary Examiner* — Nicholas Lucchesi
*Assistant Examiner* — Ian Holloway
(74) *Attorney, Agent, or Firm* — Jennifer C. Cheng; Joel B. German; Debra D. Condino (57) ABSTRACT

Apparatus and methods for implanting ocular implants in eyes are provided which include a bent cannula having a lumen extending therethrough, the lumen having a length and a diameter and being configured to receive an ocular implant. The ocular implant is made up of a plurality of substantially uniformly sized particles, preferably a plurality of uniformly sized microspheres, arranged in a one-by-one array along the length of the lumen. The apparatus further comprises a mechanism for delivering the implant through the distal end of the lumen and into the eye, preferably without the use of a liquid or gel carrier medium located in the lumen along with the implant.

20 Claims, 2 Drawing Sheets

(56) References Cited

U.S. PATENT DOCUMENTS

| | | | |
|---|---|---|---|
| 4,304,765 A | 12/1981 | Shell et al. | |
| 4,383,992 A | 5/1983 | Lipari | |
| 4,521,210 A | 6/1985 | Wong | |
| 4,597,753 A | 7/1986 | Turley | |
| 4,668,506 A | 5/1987 | Bawa | |
| 4,727,064 A | 2/1988 | Pitha | |
| 4,799,478 A | 1/1989 | Federov et al. | |
| 4,803,075 A | 2/1989 | Wallace et al. | |
| 4,846,809 A | 7/1989 | Sims | |
| 4,850,970 A | 7/1989 | Sutherland | |
| 4,853,224 A | 8/1989 | Wong | |
| 4,900,304 A | 2/1990 | Fujioka et al. | |
| 4,907,587 A | 3/1990 | Federov et al. | |
| 4,915,686 A | 4/1990 | Frederick | |
| 4,920,104 A | 4/1990 | DeVore et al. | |
| 4,941,874 A | 7/1990 | Sandow et al. | |
| 4,959,217 A | 9/1990 | Sanders | |
| 4,997,652 A | 3/1991 | Wong | |
| 5,014,717 A | 5/1991 | Lohrmann | |
| 5,059,172 A | 10/1991 | Sutherland et al. | |
| 5,098,443 A | 3/1992 | Parel et al. | |
| 5,164,188 A | 11/1992 | Wong | |
| 5,188,607 A | 2/1993 | Wu | |
| 5,219,339 A | 6/1993 | Saito | |
| 5,250,026 A | 10/1993 | Ehrlich et al. | |
| 5,256,408 A | 10/1993 | Babcock et al. | |
| 5,279,554 A | 1/1994 | Turley | |
| 5,284,479 A | 2/1994 | DeJong | |
| 5,324,718 A | 6/1994 | Loftsson | |
| 5,332,582 A | 7/1994 | Babcock et al. | |
| 5,336,206 A | 8/1994 | Shichman | |
| 5,378,475 A | 1/1995 | Smith et al. | |
| 5,443,505 A | 8/1995 | Wong et al. | |
| 5,451,213 A | 9/1995 | Teicher et al. | |
| 5,466,233 A | 11/1995 | Weiner et al. | |
| 5,476,511 A | 12/1995 | Gwon et al. | |
| 5,494,901 A | 2/1996 | Javitt et al. | |
| 5,501,856 A | 3/1996 | Ohtori et al. | |
| 5,516,522 A | 5/1996 | Peyman et al. | |
| 5,576,311 A | 11/1996 | Guyer | |
| 5,582,591 A | 12/1996 | Cheikh | |
| 5,616,123 A | 4/1997 | Cheikh | |
| 5,651,774 A | 7/1997 | Taranto et al. | |
| 5,656,026 A | 8/1997 | Joseph | |
| 5,725,521 A | 3/1998 | Mueller | |
| 5,746,718 A | 5/1998 | Steyn | |
| 5,766,242 A | 6/1998 | Wong et al. | |
| 5,770,589 A | 6/1998 | Billson et al. | |
| 5,807,400 A | 9/1998 | Chambers et al. | |
| 5,817,075 A | 10/1998 | Guingo | |
| 5,824,001 A | 10/1998 | Erskine | |
| 5,824,072 A | 10/1998 | Wong | |
| 5,869,079 A | 2/1999 | Wong et al. | |
| 5,876,373 A | 3/1999 | Giba et al. | |
| 5,941,250 A | 8/1999 | Aramant et al. | |
| 5,957,892 A | 9/1999 | Thorne | |
| 6,074,661 A | 6/2000 | Olejnik et al. | |
| 6,107,347 A | 8/2000 | Francese et al. | |
| 6,117,443 A | 9/2000 | Cherif-Cheikh | |
| 6,120,786 A | 9/2000 | Cherif Cheikh | |
| 6,142,972 A | 11/2000 | Cheikh | |
| 6,159,218 A | 12/2000 | Aramant et al. | |
| 6,190,350 B1 | 2/2001 | Davis et al. | |
| 6,217,895 B1 | 4/2001 | Guo et al. | |
| 6,251,418 B1* | 6/2001 | Ahern et al. | 424/423 |
| 6,271,216 B1 | 8/2001 | Mello et al. | |
| 6,331,313 B1 | 12/2001 | Wong et al. | |
| 6,395,294 B1 | 5/2002 | Peyman | |
| 6,407,079 B1 | 6/2002 | Muller et al. | |
| 6,450,937 B1 | 9/2002 | Mercereau et al. | |
| 6,548,078 B2 | 4/2003 | Guo et al. | |
| 6,554,760 B2 | 4/2003 | Lamoureux et al. | |
| 6,639,116 B2 | 10/2003 | Lever et al. | |
| 6,648,857 B1 | 11/2003 | Pedigo | |
| 6,699,493 B2 | 3/2004 | Wong | |
| 6,713,081 B2 | 3/2004 | Robinson et al. | |
| 6,719,750 B2 | 4/2004 | Varner et al. | |
| 6,723,353 B2 | 4/2004 | Beck et al. | |
| 6,899,717 B2* | 5/2005 | Weber et al. | 606/107 |
| 7,090,681 B2 | 8/2006 | Weber et al. | |
| 7,147,644 B2 | 12/2006 | Weber et al. | |
| 7,189,245 B2 | 3/2007 | Kaplan | |
| 7,468,065 B2 | 12/2008 | Weber et al. | |
| 7,651,505 B2 | 1/2010 | Lubock et al. | |
| 7,753,916 B2 | 7/2010 | Weber et al. | |
| 2002/0026176 A1* | 2/2002 | Varner et al. | 604/891.1 |
| 2002/0082609 A1 | 6/2002 | Green | |
| 2002/0198174 A1 | 12/2002 | Lyons | |
| 2003/0060763 A1 | 3/2003 | Penfold et al. | |
| 2003/0171320 A1 | 9/2003 | Guyer | |
| 2003/0208218 A1 | 11/2003 | Kadziauskas et al. | |
| 2004/0054374 A1 | 3/2004 | Weber et al. | |
| 2004/0057979 A1 | 3/2004 | Wong et al. | |
| 2004/0077562 A1 | 4/2004 | Chandavarkar et al. | |
| 2004/0152664 A1 | 8/2004 | Chang et al. | |
| 2004/0170665 A1* | 9/2004 | Donovan | 424/427 |
| 2004/0215133 A1 | 10/2004 | Weber et al. | |
| 2005/0032747 A1 | 2/2005 | Bartolini et al. | |
| 2005/0049605 A1 | 3/2005 | Vaquero et al. | |
| 2005/0101967 A1 | 5/2005 | Weber et al. | |
| 2005/0119737 A1 | 6/2005 | Bene et al. | |
| 2005/0154399 A1 | 7/2005 | Weber et al. | |
| 2005/0203542 A1 | 9/2005 | Weber et al. | |
| 2006/0108012 A1 | 5/2006 | Barrow et al. | |
| 2006/0173060 A1 | 8/2006 | Chang et al. | |
| 2006/0241650 A1 | 10/2006 | Weber et al. | |
| 2007/0293873 A1 | 12/2007 | Chang | 623/6.12 |
| 2008/0097335 A1 | 4/2008 | Trogden et al. | |
| 2008/0097459 A1 | 4/2008 | Kammerlannder | |

FOREIGN PATENT DOCUMENTS

| | | |
|---|---|---|
| EP | 0304700 | 3/1989 |
| EP | 0415504 | 3/1991 |
| EP | 0544948 | 9/1995 |
| EP | 1419748 | 11/2002 |
| EP | 1323450 | 7/2003 |
| WO | WO 91/12048 | 8/1991 |
| WO | WO 99/33512 | 7/1999 |
| WO | WO 99/53991 | 10/1999 |
| WO | WO 00/02564 | 1/2000 |
| WO | WO 02/089815 | 11/2002 |
| WO | WO 2004/026106 | 4/2004 |
| WO | WO 2004/069280 | 8/2004 |
| WO | WO 2004/087043 | 10/2004 |
| WO | WO 2005/055873 | 6/2005 |
| WO | WO 2006/071554 | 7/2006 |
| WO | 2008/019265 | 2/2008 |
| WO | 2008/019267 | 2/2008 |
| WO | WO 2011/002716 | 1/2011 |

OTHER PUBLICATIONS

Heller, Biodegradable Polymers in Controlled Drug Delivery, In: CRC Critical Reviews in Therapeutic Drug Carrier Systems, vol. 1, CRC Press, Boca Raton, FL 1987, pp. 39-90.

Aukunuru et al., "In Vitro Delivery of Nano- and Micro-Particles to Human Retinal Pigment Epthelial (ARPE-19) Cells", Drug Delivery Technology, vol. 2, No. 2, Mar./Apr. 2002, pp. 50-57.

Beer et al., "Intraocular Concentration and Pharmacokinetics of Triamcinolone Acetonide After a Single Intravitreal Injection", Ophthalmology, vol. 110, No. 4, Apr. 2003, pp. 681-686.

Cheng et al., "Intravitreal Sustained-Release Dexamethasone Device in the Treatment of Experimental Uveitis", Investigatative Ophthalmology & Visual Science, Feb. 1995, vol. 36, No. 2, pp. 442-453.

Crabb et al., "Cloning of the cDNAs encoding the cellular retinaldehyde-binding protein from bovine and human retina and comparison of the protein structures", J. Biol. Chem., 265(35), 1988, pp. 18688-18692.

Dunn et al., ARPE-19, a human retinal pigment epithelial cell line with differentiated properties, Exp. Eye Res 62 (1996), pp. 155-169.

(56) References Cited

OTHER PUBLICATIONS

Enyedi et al., "An Intravitreal Device Providing Sustained Release of Cyclosporine and Dexamethasone", Current Eye Research (1995) pp. 549-557.

Klimanskaya et al., "Derivation and comparative assessment of retinal pigment epithelium from human embryonic stem cells using transcriptomics", Cloning and Stem Cells 6(3), 2004, 99. 217-245.

Kochinke et al., "Biodegradable Drug Delivery System for Uveitis Treatment", Investigative Ophthalmology & Visual Science, Feb. 15, 1996, vol. 37, No. 3, 186-B98.

Rao et al., "Preparation and Evaluation of Ocular Inserts Containing Norfloxacin", Turk. J. Med. Sci. (2004) 34, pp. 239-246.

Rogojina et al., "Comparing the use of affymetrix to spotted oligonucleotide microarrays using two retinal pigment epithelium cell lines", Molecular Vision, 9, 2003, pp. 482-496.

Streilein et al., "Ocular Immune Privilege: Therapeutic Opportunities from an Experiment of Nature", Nature Review Immunology (2003), 3, pp. 879-889.

USP 23; NF 18 (1995) pp. 1790-1798.

Yeung et al., "Cytotoxicity of Triamcinolone on Cultured Human Retinal Pigment Epithelial Cells: Comparison with Dexamethasone and Hydrocortisone", Jpn. J. Ophthal., 48 (2004), pp. 236-242.

* cited by examiner

APPARATUS AND METHODS FOR IMPLANTING PARTICULATE OCULAR IMPLANTS

The present application is a continuation-in-part of U.S. Ser. No. 11/455,392 filed Jun. 19, 2006, the entire contents of which applications is incorporated herein by reference.

BACKGROUND

The present invention relates to apparatus and methods for implanting ocular implants in eyes. More particularly, the invention relates to such apparatus and methods for implanting, for example, delivering, placing, positioning and the like, particulate ocular implants in an eye, for example, at one or more of various locations in an eye, for example, a mammalian eye.

The mammalian eye is a complex organ comprising an outer covering including the sclera (the tough white portion of the exterior of the eye) and the cornea (the clear outer portion covering the pupil and iris). In a medial cross section, from anterior to posterior, the eye comprises features including, without limitation: the cornea, the anterior chamber (a hollow feature filled with a watery, clear fluid called the aqueous humor and bounded by the cornea in the front and the lens in the posterior direction), the iris (a curtain-like feature that can open and close in response to ambient light), the lens, the posterior chamber (filled with a viscous fluid called the vitreous humor), the retina (the innermost coating of the back of the eye and comprising light-sensitive neurons), the choroid (an intermediate layer providing blood vessels to the cells of the eye), and the sclera. The posterior chamber comprises approximately ⅔ of the inner volume of the eye, while the anterior chamber and its associated features (lens, iris etc.) comprise about ⅓ of the eye's inner volume.

Ocular implants containing one or more therapeutic components combined with matrix components, such as polymeric components, have been proposed for use, for example, to treat conditions/diseases of the eye. Such implants have been suggested for use at various locations in the eye, for example, in the vitreous, subconjunctivally, anterior chamber and posterior chamber of the eye.

Although such prior art implants have taken on various shapes, forms and configurations, one very useful implant form is a plurality of variously sized microparticles, e.g., microspheres and the like. For example, intravitreal injection of conventional particles, which average about 1-100 microns in size, is known and has been previously practiced. This injection of such microparticles is usually conducted using the microparticles suspended in a liquid aqueous medium. It would be advantageous to deliver the microparticles in the eye without such a liquid carrier medium.

Dry delivery in the eye of extruded, rod shaped implants, for example having diameters of about 450 microns and lengths of 3-6 millimeters, has been successfully accomplished. However, it would be highly desirable to reduce the diameter of the implant in order to allow the use of a smaller needle for injection. Reducing the diameter of such rod shaped implants often reduces the strength of the implant so that it breaks up during handling. Moreover, as such a rod shaped implant is reduced in diameter, the length of the implant gets much longer (so as to deliver an equal amount of therapeutic component to the eye) making the implant impractical for use, and even a hazard for ocular injection.

Prior attempts to dry inject microparticles in the eye have been less than completely successful. For example, without a liquid or gel carrier in the lumen containing the microparticles, the microparticles tend to become wedged between the injector assembly and the inner wall of the needle, thus preventing the assembly from delivering the full implant to the eye or causing the physician to apply excessive amounts of force to the assembly, which excessive force can be dangerous to the eye.

There continues to be a need for apparatus and methods effective to dry implant microparticles in an eye utilizing a liquid free lumen.

SUMMARY

New apparatus for implanting an ocular implant in an eye have been discovered. The present apparatus and methods are useful for placing drug delivery implants, for example, substantially biodegradable drug delivery implants, into an eye without the need for a liquid carrier medium and without causing any substantial breakage or other damage to the implant. Further, the apparatus enables dry injection of microparticles in an eye through an exceptionally small cannula or needle, thus accelerating healing and reducing invasiveness of the injection.

In one aspect of the invention, the apparatus comprises a cannula having a liquid free lumen extending therethrough, the lumen having a length and a diameter and being configured to receive an ocular implant comprising a plurality of substantially uniformly sized liquid free, or dry, particles arranged in a one-by-one (synonymously, in a single file manner) array along the length of the lumen. The apparatus further comprises a mechanism for delivering the implant through the distal end of the lumen and into the eye, preferably without the use of a liquid or gel carrier medium located in the lumen along with the implant.

In a preferred embodiment, the mechanism for delivering the implant comprises a push rod. The push rod is receivable within the lumen and is movable from a first position to a second position. In addition, the apparatus comprises a movement assembly operatively coupled to the push rod and structured to move the push rod from the first position to the second position, preferably in a controlled manner. The cannula is bent in order to hold the dry particles within the lumen before movement of the push rod to the second position.

Preferably, the diameter of the lumen is substantially uniform in size along the length of the lumen. In one aspect of the invention, the apparatus further comprises an ocular implant located in the lumen and comprising a plurality of substantially uniformly sized particles. The apparatus may include substantially no liquid material present in the lumen with the plurality of particles. In other words, the implant can be delivered into the eye in a "dry state" through a liquid free lumen.

The plurality of substantially uniformly sized particles may comprise, for example, substantially spherical particles. The substantially spherical particles are located in the lumen in a one-by-one array along the length of the lumen. As hereinabove noted, the bent cannula stabilizes the particles within the lumen prior to use.

Advantageously, the cannula has an outside diameter no larger than a standard 25 gauge needle. For example, the cannula may have an outer diameter equal to a thin-walled 27 gauge needle. The diameter of the lumen of the cannula is preferably about 350 microns or even less. For example, the lumen has a diameter in a range of about 200 microns or about 250 microns to about 300 microns or about 350 microns. In these embodiments of the invention, the particles making up the ocular implant comprise microparticles in the form of substantially uniformly sized microspheres.

Preferably, the maximum transverse dimension of each particle of the plurality of particles is at least about 70% of the diameter of the lumen, for example, is at least about 80% of the diameter of the lumen, for example is at least about 90% of the diameter of the lumen.

The particles are substantially uniform in size. For example, the plurality of particles includes a smallest particle and a largest particle having a maximum transverse dimension within about 20%, preferably about 10%, more preferably about 5%, of the maximum transverse dimension of the smallest particle.

The plurality of particles located in the lumen includes a number of particles in a range of about 10 or about 25 to about 150 or about 200. The use of particles with a variation or range of particle size is enabled by the bent cannula.

In some embodiments, the plurality of particles comprises includes particles having different compositions, for example, in the same or different proportions relative to one another.

In embodiments of the invention comprising a push rod for delivering the plurality of particles, the push rod and cannula may be configured so that the push rod comes into physical contact with at least one particle of the plurality of particles in moving from the first position to the second position. For example, the push rod and cannula are configured so that the push rod comes into direct physical contact with only one particle of the plurality of particles in moving from the first position to the second position.

In another aspect of the invention, the plurality of particles comprises compositions including at least one therapeutic component effective to provide a therapeutic effect when released into an eye, and a biodegradable component, a non-biodegradable component, and combinations thereof.

For example, the plurality of particles further comprises a biodegradable polymer in combination with the at least one therapeutic component.

Methods for implanting an ocular implant in an eye are also provided. The methods generally comprise the steps of providing an apparatus such as the apparatus described elsewhere herein.

For example, an apparatus useful in the present methods comprises a cannula having a distal end and a lumen extending therethrough and the lumen has a length and a diameter and contains an ocular implant comprising a plurality of substantially uniformly sized particles in a one-by-one array along the length of the lumen. The apparatus further comprises a push rod positioned to be received within the lumen and movable from a first position to a second position, and a movement assembly operatively coupled to the push rod and structured to move the push rod from the first position to the second position.

The method further comprises the step of placing, for example, after sterilization of the apparatus, the distal end of the cannula in a position so that the plurality of particles passing from the lumen out of the distal end are provided at a desired location in an eye. Additionally, the method comprises operating the movement assembly to move the push rod from the first position to the second position, thereby causing the plurality of particles to pass from the lumen through the distal end and into a target location in the eye. The operating step may be a manual operating step.

The present apparatus and methods can be practiced to treat a condition of the posterior segment of a mammalian eye, such as a condition selected from the group consisting of macular edema, dry and wet macular degeneration, choroidal neovascularization, diabetic retinopathy, acute macular neuroretinopathy, central serous chorioretinopathy, cystoid macular edema, and diabetic macular edema, uveitis, retinitis, choroiditis, acute multifocal placoid pigment epitheliopathy, Behcet's disease, birdshot retinochoroidopathy, syphilis, lyme, tuberculosis, toxoplasmosis, intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; retinal arterial occlusive disease, anterior uveitis, retinal vein occlusion, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemiretinal vein occlusion, papillophlebitis, central retinal artery occlusion, branch retinal artery occlusion, carotid artery disease (CAD), frosted branch angiitis, sickle cell retinopathy, angioid streaks, familial exudative vitreoretinopathy, and Eales disease; traumatic/surgical conditions such as sympathetic ophthalmia, uveitic retinal disease, retinal detachment, trauma, photocoagulation, hypoperfusion during surgery, radiation retinopathy, and bone marrow transplant retinopathy; proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; punctate inner choroidopathy, acute posterior multifocal placoid pigment epitheliopathy, myopic retinal degeneration, acute retinal pigment epithelitis, retinitis pigmentosa, proliferative vitreal retinopathy (PVR), age-related macular degeneration (ARMD), diabetic retinopathy, diabetic macular edema, retinal detachment, retinal tear, uveitis, cytomegalovirus retinitis and glaucoma comprises administering to the posterior segment of the eye a composition comprising an SIRT1-activating agent in an ophthalmically effective vehicle. Conditions treated with the present apparatus and methods may be ophthalmic conditions involving ocular degeneration, such as neurodegeneration of retinal ganglion cells.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying drawings.

DESCRIPTION

As described herein, administration of a therapeutic agent through the use of one or more intraocular implants comprising a plurality of substantially uniformly sized particles may improve treatment of undesirable ocular conditions.

DEFINITIONS

For the purposes of this description, we use the following terms as defined in this section, unless the context of the word indicates a different meaning.

As used herein, an "intraocular implant" refers to a device or element that is structured, sized, or otherwise configured to be placed in an eye. Intraocular implants are generally biocompatible with physiological conditions of an eye and do not cause adverse side effects. Intraocular implants may be placed in an eye without disrupting vision of the eye.

As used herein, a "therapeutic component" refers to a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in an eye.

As used herein, a "drug release sustaining component" refers to a portion of the intraocular implant that is effective to provide a sustained release of the therapeutic agents of the implant. A drug release sustaining component may be a biodegradable polymer matrix, or it may be a coating covering a core region of the implant that comprises a therapeutic component.

As used herein, "associated with" means mixed with, dispersed within, coupled to, covering, or surrounding.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "biodegradable polymer" refers to a polymer or polymers which degrade in vivo, and wherein erosion of the polymer or polymers over time is required to achieve release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

The term "treat", "treating", or "treatment" as used herein, refers to reduction or resolution or prevention of an ocular condition, ocular injury or damage, or to promote healing of injured or damaged ocular tissue.

The term "therapeutically effective amount" as used herein, refers to the level or amount of agent needed to treat an ocular condition, or reduce or prevent ocular injury or damage without causing significant negative or adverse side effects to the eye or a region of the eye.

Figure 1:
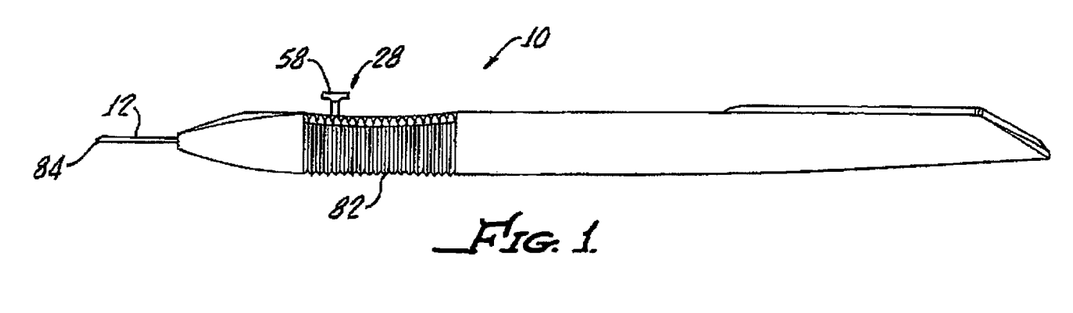
FIG. 1 is a cross sectional view of an apparatus in accordance with the invention, the apparatus including a cannula for implanting an ocular implant in a region of a mammalian eye.

With reference to FIG. 1, an apparatus for implanting an ocular implant in an eye in accordance with the invention is shown generally at 10. The apparatus 10 comprises a cannula 12 having a lumen extending therethrough.

Figure 2:
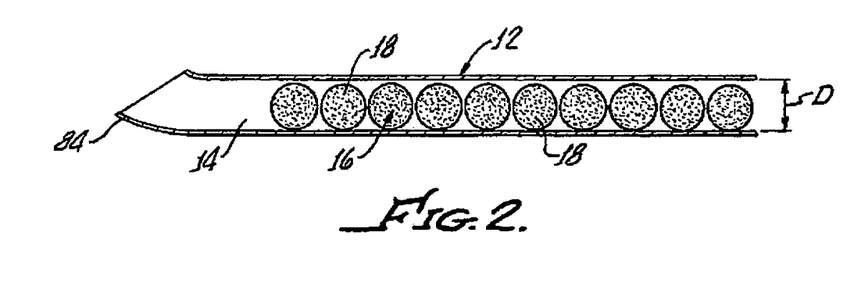
FIG. 2 is a cross sectional view of the cannula of the apparatus shown in FIG. 1, the cannula with a bent top and having a liquid free lumen containing an ocular implant comprising a plurality of substantially uniformly sized particles, in accordance with certain aspects of the present invention.

FIG. 2 is a simplified view of a cross section of the cannula 12 of apparatus 10. As shown, lumen 14 of cannula 12 has a length and a diameter D and is configured to receive an ocular implant 16 comprising a plurality of substantially uniformly sized particles 18 in a one-by-one array along the length of the lumen 14. The diameter D is substantially uniform in size along the length of the lumen. A slight bend 84 is incorporated into the cannula 12 to provide an engagement with the particles sufficient to hold the implants 16 in place.

In one aspect of the invention, the apparatus 10 further comprises an ocular implant, such as ocular implant 16, comprising a plurality of substantially uniformly sized particles, such as microparticles 18, located in the lumen 14 in a one-by-one array along the length of the lumen 14.

The particles which make up the implant 16 preferably comprise a composition comprising a therapeutic component and a polymeric component for controlling release of the therapeutic component from the particle. Suitable polymeric materials or compositions for use in the polymeric components of the particles of the present invention include those materials which are compatible, that is biocompatible, with the eye so as to cause no substantial interference with the functioning or physiology of the eye. Such materials preferably are at least partially and more preferably substantially completely biodegradable or bioerodible. Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present invention, and that disclosure is specifically incorporated herein by reference.

Of additional interest are polymers of hydroxyaliphatic carboxylic acids, either homopolymers or copolymers, and polysaccharides. Included among the polyesters of interest are polymers of D-lactic acid, L-lactic acid, racemic lactic acid, glycolic acid, polycaprolactone, and combinations thereof. Generally, by employing the L-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, etc.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the particles suitable for use in the present invention may include biocompatibility, compatibility with the therapeutic component, ease of use of the polymer in making the implants of the present invention, a half-life in the physiological environment of at least about 6 hours, preferably greater than about one day, not significantly increasing the viscosity of the vitreous, and water insolubility.

The biodegradable polymeric materials which are included in the particles are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, where the polymers may be employed as varying layers or mixed.

The implant 16 advantageously is structured to have a lifetime at least equal to the desired period of therapeutic component administration in the eye, and may have lifetimes of about 5 to about 10 times the desired period of administration. The period of administration may be at least about 3 days, at least about 7 days, at least about 15 days, at least about 20 days, at least about 30 days or longer.

The therapeutic component useful in the implants may include any suitable pharmacologically active agent or therapeutic agent for which sustained release, for example, in the eye, is desirable. Advantageously, the therapeutic component is sufficiently soluble in region of the eye in which the implant is to be placed, for example, in the vitreous of the eye, such that it will be present at a pharmacologically or therapeutically effective dose.

Pharmacological or therapeutic agents of interest include hydrocortisone (5-20 mcg/l as plasma level), gentamicin (6-10 mcg/ml in serum), 5-fluorouracil (about 0.30 mg/kg body weight in serum), sorbinil, IL-2, TNF, Phakan-a (a component of glutathione), thiola-tiopronin, Bendazac, acetylsalicylic acid, trifluorothymidine, interferon (alpha., beta. and gamma.), immune modulators, e.g. lymphokines, monokines, and growth factors, etc.

Pharmacological or therapeutic agents of particular interest include, without limitation, anti-glaucoma drugs, such as the beta-blockers, such as timolol maleate, betaxolol and metipranolol; mitotics, such as pilocarpine, acetylcholine chloride, isofluorophate, demecarium bromide, echothiophate iodide, phospholine iodide, carbachol, and physostigmine; epinephrine and salts, such as dipivefrin hydrochloride; and dichlorphenamide, acetazolamide and methazolamide; anti-cataract and anti-diabetic retinopathy drugs, such as aldose reductase inhibitors, such as tolrestat, lisinopril, enalapril, and statil; thiol cross-linking drugs other than those considered previously; anti-cancer drugs, such as retinoic acid, methotrexate, adriamycin, bleomycin, triamcinolone, mitomycin, cis-platinum, vincristine, vinblastine, actinomycin-D, ara-c, bisantrene, CCNU, activated cytoxan, DTIC, HMM, melphalan, mithramycin, procarbazine, VM26, VP16, and tamoxifen; immune modulators, other than those indicated previously; anti-clotting agents, such as tissue plasminogen activator, urokinase, and streptokinase; anti-tissue damage agents, such as superoxide dismutase; proteins and nucleic acids, such as mono- and polyclonal antibodies, enzymes, protein hormones and genes, gene fragments and plasmids; steroids, particularly anti-inflammatory or anti-fibrous drugs, such as cortisone, hydrocortisone, prednisolone, prednisone, dexamethasone, progesterone-like compounds, medrysone (HMS) and fluorometholone; non-steroidal anti-inflammatory drugs, such as ketorolac tromethamine, diclofenac sodium and suprofen; antibiotics, such as loridine (cephaloridine), chloramphenicol, clindamycin, amikacin, tobramycin, methicillin, lincomycin, oxacillin, penicillin, amphotericin B, polymyxin B, cephalosporin family, ampicillin, bacitracin, carbenicillin, cephalothin, colistin, erythromycin, streptomycin, neomycin, sulfacetamide, vancomycin, silver nitrate, sulfisoxazole diolamine, and tetracycline; other antipathogens, including anti-viral agents, such as idoxuridine, trifluorouridine, vidarabine (adenine arabinoside), acyclovir (acycloguanosine), pyrimethamine, trisulfapyrimidine-2, clindamycin, nystatin, flucytosine, natamycin, miconazole and piperazine derivatives, e.g. diethylcarbamazine; cycloplegic and mydriatic agents, such as atropine, cyclogel, scopolamine, homatropine and mydriacyl; and the like and mixtures thereof.

Other agents useful in the systems of the present invention include, without limitation, anticholinergics, anticoagulants, antifibrinolytic agents, antihistamines, antimalarials, antitoxins, chelating agents, hormones, immunosuppressives, thrombolytic agents, vitamins, salts, desensitizing agents, prostaglandins, amino acids, metabolites, antiallergenics, and the like and mixtures thereof.

In some embodiments of the invention, the implants are suitable for treating inflammation-mediated conditions of the eye. The term "inflammation-mediated condition of the eye" is meant to include any condition of the eye which may benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic uveitis, proliferative vitreoretinopathy (PVR), sympathetic ophthalmia, Vogt Koyanagi-Harada (VKH) syndrome, histoplasmosis, and uveal diffusion.

For example, the implant 16 may comprise a plurality of substantially uniformly sized microparticles 18 structured for being implanted into the vitreous of the eye wherein the therapeutic component of at least one or more of the particles comprises a steroidal anti-inflammatory agent, for example but not limited to, dexamethasone, and a bioerodible polymer, for example a polylactic acid polyglycolic acid (PLGA) copolymer. The plurality of particles 18, when implanted in an eye, preferably delivers the therapeutic agent to the vitreous in an amount sufficient to reach a concentration equivalent to at least about 0.05 µg/ml dexamethasone within about 48 hours and maintain a concentration equivalent to at least about 0.03 µg/ml dexamethasone for at least about three weeks. In another embodiment of the invention, the implant 16 preferably delivers the agent to the vitreous in an amount sufficient to reach a concentration equivalent to at least about 0.2 µg/ml dexamethasone within about 6 hours and maintains a concentration equivalent to at least about 0.01 µg/ml dexamethasone for at least about three weeks.

"A concentration equivalent to dexamethasone", as used herein, refers to the concentration of a steroidal anti-inflammatory agent necessary to have approximately the same efficacy in vivo as a particular dose of dexamethasone. For example, hydrocortisone is approximately twenty-fivefold less potent than dexamethasone, and thus a 25 mg dose of hydrocortisone would be equivalent to a 1 mg dose of dexamethasone. One of ordinary skill in the art would be able to determine the concentration equivalent to dexamethasone for a particular steroidal anti-inflammatory agent from one of several standard tests known in the art. Relative potencies of selected corticosteroids may be found, for example, in Gilman, A. G., et al. eds. (1990). *Goodman and Gilman's: The Pharmacological Basis of Therapeutics*. 8th Edition, Pergamon Press: New York, p. 1447, which is incorporated herein by this specific reference.

In other embodiments, the implant 16 delivers the agent to the vitreous in an amount sufficient to reach a concentration equivalent to at least about 0.3 µg/ml, or at least about 0.5 µg/ml, or at least about 0.75 µg/ml, or at least about 1.0 µg/ml, or at least about 2.0 µg/ml dexamethasone within about 4 hours, or within about 6 hours, or within about 8 hours, or within about 10 hours, or within about 24 hours.

A concentration equivalent to at least about 0.01 µg/ml, or at least about 0.02 µg/ml, or at least about 0.03 µg/ml, or at least about 0.05 µg/ml, or at least about 0.07 µg/ml dexamethasone may be maintained for an extended period of time (e.g., at least about three weeks or longer). The preferred concentration levels of therapeutic component or drug in the vitreous may vary according to the inflammatory mediated condition being treated. For example, for treating uveitis, a concentration equivalent of at least about 0.01 to 0.1 µg/ml dexamethasone is preferred.

In one embodiment, the concentration of therapeutic component is maintained for least about four weeks. In other embodiments, the concentration is maintained for at least about five weeks, or at least about six weeks, or at least about seven weeks, or at least about eight weeks, or at least about nine weeks, or at least about 10 weeks, or at least about 12 weeks or longer. The preferred duration of therapeutic component or drug release may be determined by the inflammatory mediated condition being treated. For treating uveitis, a drug release duration of at least about three weeks is preferable, more preferably at least about four weeks. In one embodiment, more than one implant 16 may be sequentially implanted into the vitreous, for example in different locations in the vitreous, in order to maintain therapeutic component or drug concentrations for even longer periods.

The formulation of the implants in accordance with the present invention may vary according to the desired therapeutic component release profile, the particular therapeutic component used, the condition being treated, and the medical history of the patient.

Copolymers of glycolic and lactic acid are of particular interest, where the rate of biodegradation is controlled by the ratio of glycolic to lactic acid. The % of polylactic acid in the polylactic acid polyglycolic acid (PLGA) copolymer can be 0-100%, preferably about 15-85%, more preferably about 35-65%. In a particularly preferred embodiment, a 50/50 PLGA copolymer is used. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries.

Selection of an effective size of the particles 18 of the implant 16 can be used to control the rate of release, period of treatment and drug concentration in the eye.

Moreover, because the implant 16 comprises a plurality of substantially uniformly sized particles, the particles themselves may be made up of different compositions, one from the other. For example, a single implant may comprise one or more particles comprising a first therapeutic component, and one or more other particles comprising a second therapeutic component that is different from the first therapeutic component. Implants made up of various differently composed particles, in different proportions, can be employed to treat the eye.

In some situations, the implant 16 comprises a plurality of different particles 18 having the same or different therapeutic agent, and the same or different release rates and/or delayed release rates. For example, 2, 3, 4 or more different particles can make up an implant. In this way, in a single administration a course of drug treatment may be achieved, where the pattern of release may be greatly varied. For example, a biphasic or triphasic release profile may be achieved with a single administration of an implant comprising a plurality of substantially uniformly sized microparticles having different compositions and/or the same compositions in different proportions.

Various techniques may be employed to produce the particles making up the implants described and shown herein. Useful techniques include, but are not necessarily limited to, extrusion methods, co-extrusion methods, carver press method, die cutting methods, heat compression, combinations thereof and the like. Techniques for producing the cores 22 of the elements 20 include, but are not necessarily limited to, solvent-evaporation methods, phase separation methods, interfacial methods and the like.

Production of uniformly sized particles may be achieved by conventional techniques, such as sieving and the like, that are effective to separate, from a large number of non-uniformly sized particles, a plurality of particles of uniform size. More preferably, the production of uniformly sized microspheres is accomplished using microfluidic techniques for producing "precision" microparticles.

Figure 3A:
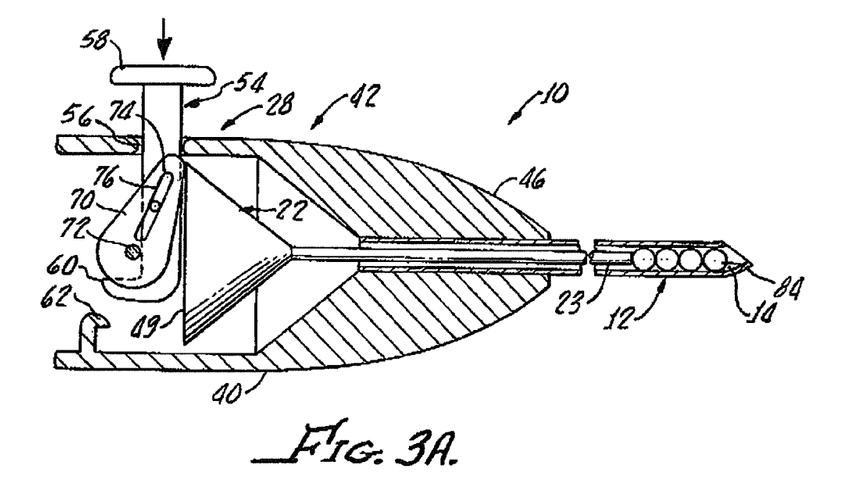
FIGS. 3A and 3B are simplified cross-sectional views of the apparatus shown in FIG. 1.
Figure 3B:
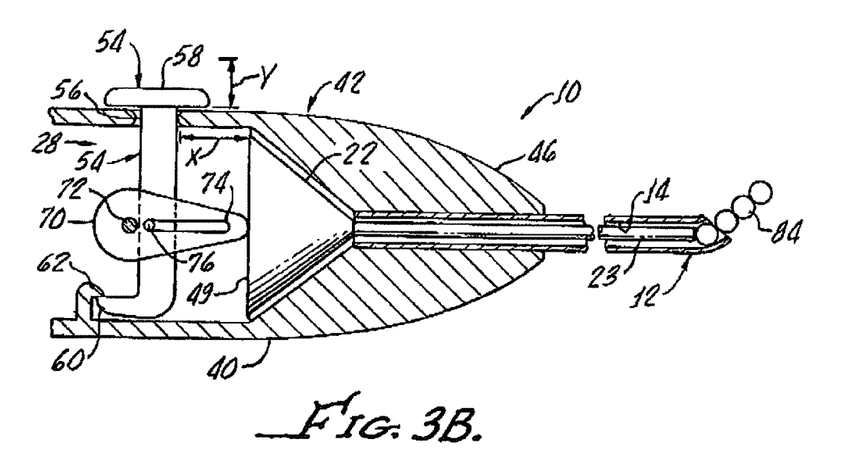

Turning now to FIGS. 3A and 3B, the apparatus 10 preferably includes a push rod 22 receivable within the lumen 14 and movable from a first position, such as illustrated in FIG. 3A, to a second position, such as illustrated in FIG. 3B.

The apparatus 10 further comprises a movement assembly 28 operatively coupled to the push rod 22 and structured to move the push rod 22 from the first position to the second position.

In the specific embodiment shown, the apparatus 10 includes housing 40 and cannula assembly 42. Cannula assembly 42 includes the cannula 12 disposed within and extending from a nose portion 46, and the push rod 22 that is slidably received with the cannula 12 and terminates at its proximal end in a cone 49 which is disposed in the interior of the housing 40. The movement assembly 28 includes a lever 54 is mounted for movement normal to the longitudinal axis of the apparatus 10. One end of the lever extends from the apparatus 10 through opening 56 and terminates in button 58. The other end of the lever 54 includes tab 60 which is engageable with latch 62 on housing 40. The tab 60 and latch 62 can be configured to engage in a snap-fit relationship. Cam 70 is disposed within housing 40 and is pivotally mounted to the housing about pivot 72 which is located distally relative to lever 54. Slot 74 is provided on cam 70. Pin 76 on lever 54 is slidably retained within slot 74. The end of cam 70 is located proximal to the cone 49 of push rod 22.

In the undeployed condition depicted in FIG. 3A, implant 16, comprising plurality of substantially uniform microspheres 18, is retained in the lumen 14 distal of a push rod end 23, a bend in the cannula 12 stabilizes the microspheres 18 therein. Manual depression of button 58 causes downward movement of lever 54 normal to the longitudinal axis of the apparatus 10. This movement exerts a force onto cam 70 which is transmitted by way of pin 76 of the lever to slot 74 of the cam 70, causing rotational movement of cam 70 about pivot 72. With the end of cam 70 in approximation to cone 49, such rotation of the cam 70 causes the end of the cam 70 to engage cone 49, causing translational movement of push rod 22 relative to the cannula 12. This translational movement of the push rod 22, in turn, ejects the implant 16 from the cannula 12, as depicted in FIG. 12B past the bend 84. When the lever 54 is fully depressed and the implant ejected, tab 60 engages latch 62, thereby locking the assembly 28 into a depressed, post-ejection, condition.

An advantage of this structure of apparatus 10 is that it provides for a smooth, controlled ejection of the implants 16. This smooth ejection is enabled by the bend 84 in the cannula 12 which prevents flow of uncontrolled implant 16 due to inertia which would otherwise occur if the bend 84 were not present, the bend 84 providing a small resistance to flow, or movement, of the implant 16 when not urged by the push rod 22. By "controlled" it is meant that the force applied to the implant for ejection is proportional to the force applied by the user to actuate the apparatus. The user has direct feedback as to the rate of ejection and can dynamically adjust the force being delivered to the linkage to obtain the desired ejection rate. In addition, depending in particular linkage configurations and dimensions, the apparatus 10 can be configured such that the range of translational movement of the plunger along the longitudinal, or "x" axis, of the housing can be significantly longer, although still proportional to, the range of movement of the actuator along the normal or "y" axis.

Other actuating mechanisms are contemplated and the present invention is not limited to the specific apparatus shown. Other suitable apparatus are described and shown in Weber et al. U.S. Pat. No. 6,899,717, the entire disclosure of which is incorporated herein by this reference.

As mentioned elsewhere herein, preferably, the implants useful in the present invention comprise a plurality of substantially uniformly sized microspheres, sometimes referred to in the industry as precision microparticles. The microspheres are made up of a pharmaceutically acceptable polymeric composition and one or more pharmaceutically active agents, for example, steroids, and are effective to provide a therapeutically effective dosage of the agent or agents directly to a region of the eye to treat one or more undesirable ocular conditions.

An intraocular implant in accordance with the disclosure herein comprises a therapeutic component and a pharmaceutically acceptable polymeric component associated with the therapeutic component. In accordance with a specific embodiment of the present invention, the therapeutic component comprises, consists essentially of, or consists of, an alpha-2 adrenergic receptor agonist. In addition, the polymeric component may be associated with the therapeutic component in an amount or may be comprised of a composition effective to sustain release of a therapeutically effective amount of the active agent into an eye in which the implant is placed.

Intraocular implants have been developed which can release drug loads over various time periods. These implants, which when inserted into an eye, such as the vitreous of an eye, provide therapeutic levels of an alpha-2 adrenergic receptor agonist for extended periods of time (e.g., for about 1 week or more). The implants disclosed are effective in treating ocular conditions, such as posterior ocular conditions.

In one embodiment of the present invention, an intraocular implant comprises a biodegradable polymer matrix. The biodegradable polymer matrix is one type of a drug release sustaining component. The biodegradable polymer matrix is effective in forming a biodegradable intraocular implant. The biodegradable intraocular implant comprises an alpha-2 adrenergic receptor agonist associated with the biodegradable polymer matrix. The matrix degrades at a rate effective to sustain release of an amount of the alpha-2 adrenergic receptor agonist for a time greater than about one week from the time in which the implant is placed in ocular region or ocular site, such as the vitreous of an eye.

Turning back to FIG. 2, the plurality of particles are substantially spherical, and are substantially uniform in size. Recent advances in microfluidics have made possible the manufacture of micron-sized drug-containing polymeric spheres in accordance with great precision in size. Barrow et al., United States Patent Application Publication No. 2006/0108012, the entire disclosure of which is incorporated herein by this reference, discloses microfluidic devices and methods for producing sphere-like droplets of highly precise and repeatable dimensions. The plurality of particles located in the lumen includes a number of particles in a range of about 10 or about 25 to about 150 or about 200, or more.

The advantages of the present invention are numerous. For example, the size uniformity of the microspheres 18 ensures that they will not jam in the cannula as they pass from the lumen. The implant 16 is injected as a flexible string of beads, as opposed to a rigid cylindrical rod, and therefor will fit more conveniently in any location in the eye. For example, the implant can be implanted in a curved configuration in the eye.

In addition, in one particularly useful aspect of the invention, the microparticles provide the ability to load different drugs into different microspheres and/or individually design the drug release rate for each microsphere by varying polymer composition, drug content, or the processing conditions. Dosages may be administered with greater precision than can be accomplished with a conventional intraocular implant, for example, a conventional cylindrically shaped implant.

It is desirable, although not necessary, to use a cannula that corresponds in dimensions to a 21 or 22 gauge needle, and more preferably, an even smaller needle. Such a small cannula has the important advantage that punctures made by such small bore needle or cannula according to techniques described herein are self-sealing. In the present application, this becomes advantageous in that the implant delivery into the eye can be accomplished without the need for suturing the puncture site, as would be necessary were a larger gauge needle used. We have determined that by using a 21 or 22 gauge cannula or smaller, the implant can be placed and the cannula withdrawn without excessive fluid leakage from the eye, despite the normal fluid pressures within the eye, and stitching of the puncture site can be avoided. 21 gauge needles have outer diameters of approximately 0.032 inches. Thin wall or extra thin wall versions of 21 gauge needles can have inner diameters of approximately 0.023 to 0.026 inches. 22 gauge needles have outer diameters of approximately 0.028 inches, and thin wall or extra thin wall versions of 22 gauge needles have inner diameters of approximately 0.019 to 0.023 inches. Ideally a cannula corresponding in dimensions up to those of 22 or 23 gauge, thin wall needles are used. Microimplants are dimensioned to have outer diameters to be received within the needle cannulas with sufficient tolerances to be readily pushed through the cannula. For example and without being so limited, microimplants with a diameter of 0.018 inches can be easily delivered through a 22 gauge thin wall needle, and a microimplant with a diameter of 0.015 inches is easily deliverable through a 23 gauge thin wall needle. The invention further contemplates the use of cannulas having non-circular cross-sections, including oval or elliptical cross-sections. For such non-circular cross-sectional cannulas, it is desirable that the cross-sectional area correspond to that of a circular cannula having up to a 0.032 inch diameter, that is, a cross-sectional area up to 0.0008 square inches or more, depending on the particular cross-sectional geometry.

In addition to cannula dimensions, additional modifications to both the cannula tip and in particular methods of insertion can further aid successful self-sealing methods of implantation. A typical problem when inserting a cannula into any tissue is the phenomena of "coring" of the tissue, where the insertion actually cuts a cylindrical section of tissue that enters the cannula lumen. Such coring when it occurs in the eye can exacerbate leakage of eye fluid through the injection site. By approaching the eye tissue at more of an angle relative to normal, there is a better opportunity for the cannula tip to penetrate and separate through the tissue layers and reduce coring of the tissue. Additional techniques to further reducing coring and/or excessive leakage are further described herein.

The cannula tip itself also can be configured to reduce coring phenomena, for instance, by sharpening certain portions of the bevel tip and dulling others. One skilled in the art will appreciate that the particular site of entry and the distance the cannula is inserted will depend on the particular application and the desired final location of the implant. As can also be appreciated, the ability provided herein to provide for a self-sealing method for delivering implants, has enormous impact on the ability of physicians and healthcare workers to treat diseases of the eye, because it obviates in most situations the necessity of surgery facilities, and accompanying surgical support, currently required by conventional methods.

To administer an implant comprising a plurality of substantially uniformly sized microspheres, using, e.g., the implant delivery apparatus 10 of FIG. 1, the user can grasp apparatus 10 between the thumb and middle finger along tactile ridges 82, and position the apparatus 10 near the desired point of entry into the patient's eye. The patient typically will be under a topical or local anesthetic. The user can then advance cannula 12 into the patient's eye to the desired depth, and depress ejector button 58 of the movement assembly 28 to eject the implant at the desired location. The cannula 12 is then withdrawn. Specific techniques for cannula advancement, including angles of orientation of the cannula and the bevel are further discussed herein. Where cannula 12 is dimensioned to receive and retain an implant comprising microspheres, as previously discussed, the resultant puncture site can self-seal upon withdrawal of the cannula 12. Otherwise, in situations where a larger cannula and implant are used, the puncture site can be closed up by known methods, such as suturing.

Implantations methods can also be performed without the inventive apparatus, albeit less conveniently. In such a method, a cannula having dimensions corresponding to those described above can be provided attached to a suitable holder, such as, e.g., a typical needle and syringe assembly. The implant is loaded and retained within the cannula lumen, and a push rod is further provided with the distal end received through the proximal end of the cannula lumen and positioned adjacent the implant. The distal end of the push rod remains outside the cannula and manually accessible. This assembly is then brought into position near the patient's eye, and the cannula is then used to puncture through the outer layer of a patient's eye and the cannula is further advanced a desired location within the patient's eye for deposition of the implant. Once the cannula is positioned, the push rod is moved from the proximal end of the cannula toward the distal end of the cannula, thereby ejecting the implant from the cannula. After ejection, the cannula and push rod are withdrawn from the patient's eye, and the puncture created by the insertion of the cannula into the patient's eye is self-sealing upon the removal of the cannula.

For placement e.g. in the vitreous cavity of the eye, useful implantation methods include advancing the cannula through the pars plana at a location approximately 3.5-4 mm from the limbus of the eye. For smaller diameter needles, e.g., 25 gauge or smaller, the needle can be inserted from any angle relative to the eye and still produce acceptable self-sealing results. For larger gauge needles, e.g., 23 gauge and above, self-sealing results can be enhanced by inserting the needle at angle relative to the eye surface. For example, good results are achieved by inserting the angle at an angle of 45° or less relative to the eye surface. Also, slightly improved results can be seen in some cases by orienting the bevel of the needle downward with respect to the eye surface. Another advantageous method involves a so-called "tunnel technique" approach. In this technique, the patient's eye is restrained from moving using e.g. a cotton swab or forceps, and the needle is advanced into the sclera at an angle approaching parallel relative to the eye surface. In this technique, the bevel will usually be oriented upward with respect to the eye surface. Once the tip is advanced sufficiently far enough into the scleral layer, usually such that the bevel portion is at least disposed within the scleral layer, the angle of the needle is adjusted to a more downward angle into the eye, and the needle is further advanced. Using such methods, with the shallower angle of insertion, yields wound edges that close up and seal more readily. Without being bound by theory, it is believed that insertion of the needle by this technique creates a scleral "flap" that, under intraocular pressure of the eye, is forced upward and pressed against the wound path to more effectively close up the wound.

In addition, the direction of insertion of the needle relative to the limbus of eye can have further implications upon the deposition of the implant in the vitreous cavity. For example, advancement of the needle posteriorly of the limbus or even circumferentially relative to the limbus usually provides for a suitable and acceptable location for deposition of the implant. On the other hand, advancement of the needle anteriorly of the limbus requires some caution, as it can lead to placement of the implant close to the lens of the eye, which may cause some complications.

As mentioned elsewhere herein, implants that are compatible with loading and ejection from apparatus according to the present invention can be formed by a number of known methods, including phase separation methods, interfacial methods, extrusion methods, compression methods, molding methods, injection molding methods, heat press methods and the like. Particular methods used can be chosen, and technique parameters varied, based on desired implant size and drug release characteristics. For implants described herein which comprise a plurality of substantially uniformly sized particles, preferably microspheres, which can be delivered through cannulas corresponding to a 21 gauge needle or smaller, and which therefore have cross-sectional diameters of 0.026 inches or less, or similar cross-sectional areas, microfluidic techniques are useful. Extrusion methods, as well as injection molding, compression molding, and tableting methods, may also be effective to achieve the small cross-sectional diameters or areas required of microspheres.

In manufacturing an apparatus according to the invention, it may be desirable to pre-load the implant into the cannula. Pre-loaded apparatus provide added convenience for the user and avoid unnecessary handling of implants. Further, such loading can be done under sterile conditions, thereby ensuring delivery of a sterilized implant. For the embodiment of the apparatus shown, the implant can be pre-loaded into the cannula assembly and the loaded cannula assembly incorporate into the nose cone. In this fashion, loaded nose cone/cannula assemblies can be pre-assembled, for later incorporation with the housing assembly. Label plates, or other locations on the housing, can include the appropriate information relative to particular implant loaded. Given this interchangeability, unique apparatus for the delivery of selected implants can be easily manufactured, simply by providing the particular cannula, plunger, and linkage system for the selected implant. The remaining components of the apparatus remain the same. The name plate or housing itself can be labeled to correspond to the selected implant, thus identifying the apparatus with the loaded implant.

When the apparatus is assembled with the implant pre-loaded, it may further be desirable that the implant be positioned just proximal of the opening at the cannula tip. In this fashion, the introduction of air into the eye can be avoided when the implant is ejected, as could otherwise occur were the implant located further within the cannula lumen and an air bubble or air pocket allowed to exist between the cannula tip and the implant and ejection of the implant were to force the air bubble or air pocket into the eye. One method to accomplish this is to load the implant distally into the cannula followed by the plunger, with the plunger length designed to push the implant to the desired pre-actuation position. When the cannula assembly is then installed onto the housing, the plunger and thus the implant is advanced to the desired position. As hereinabove noted, to guard against inadvertent premature release of the implant, the cannula can have a slight bend 84 incorporated into the tip such that enough friction exists between the inner wall of the cannula and the implant to hold the implant in place, but at the same time, the frictional force is easily overcome by action of the plunger to eject the implant upon actuation of the apparatus.

Other cannula designs can likewise achieve the desired effect of avoiding the introduction of air into the eye upon ejection of the implant. For example, the implant can be positioned proximally of the cannula tip but with sufficient tolerance between the implant and cannula wall to provide for air exhaust past the implant as it is moved through the cannula. Adequate tolerances are those that retain air in front of the implant at close to ambient pressure as the implant is moved along the cannula. Because fluid pressure within the eye is typically slightly positive relative to ambient pressure, air at ambient pressure will not enter the eye.

Loaded apparatus according to the invention can be packaged to include a safety cap extending over the cannula and securing to the housing. This will provide a measure of safety during handling of the apparatus. The button or other depression mechanism of the apparatus can also include a notch which receives the rim of the safety cap. In this configuration, the safety cap will then also operate to guard against unintentional depression of the button or other depression mechanism and ejection of the implant.

As can be appreciated, an apparatus according to the invention that is provided loaded with the desired implant is of great benefit to the physician user. Such apparatus can be provided sterile packaged for a single use application. The user need not ever handle the implant itself. As previously mentioned, the apparatus provides for a controlled ejection of the implant. The configuration and design of the apparatus also helps to achieve uniform placement of implants from patient to patient. Further, when the apparatus is configured to deliver a micro-implant, the apparatus provides a self-sealing method for delivery, as previously discussed. This has enormous benefit to the physician and patient in that the entire implant procedure can safely, easily, and economically be performed in a physician's office, without the need for more costly surgical support currently required for implant delivery.

EXAMPLES

The following examples illustrate embodiments of the invention.

Example 1

Microspheres are made with 40% poly-d,l-lactide-co-glycolide (Boehringer-Ingelheim 752H) and 60% dexamethasone having a uniform diameter of 280±5 µm. Each microsphere has about 0.0083 mg dexamethasone. An applicator with a thin-walled 25-g needle (i.d.=0.3 mm) can be filled with about 85 microspheres to reach a total drug content of about 0.7 mg. Total length of loaded microspheres in the needle is 23.8 mm, compared to 15.8 mm of a thermally extruded rod with a 280 µm diameter and 0.7 mg dexamethasone. The microspheres can be injected intravitreally and the drug is released over a period of three months.

Example 2

In batch 1, microspheres are made with 40% poly-d,l-lactide-co-glycolide (Boehringer-Ingelheim 752H) and 60% dexamethasone having a uniform diameter of 280±5 µm. Each microsphere has about 0.0083 mg dexamethasone. Separately in batch 2, microspheres are made with 40% poly-d, l-lactide (Boehringer-Ingleheim 203S) and 60% dexamethasone having a uniform diameter of 280±5 µm. Each microsphere has about 0.0083 mg dexamethasone. An applicator with a thin-walled 25-g needle (i.d.=0.3 mm) can be filled with about 42 microspheres from batches 1 and 2 to reach a total drug content of about 0.7 mg. Total length of loaded microspheres in the needle is 23.8 mm, compared to 15.8 mm of a thermally extruded rod with a 280 µm diameter and 0.7 mg dexamethasone. The microspheres can be injected intravitreally and the drug is released over a period of three months from half of the microspheres and from month 3 to month 6 from the other half of the microspheres.

Example 3

Microspheres are made with 80% poly-d,l-lactide-co-glycolide (Boehringer-Ingelheim 752H) and 20% cyclosporine having a uniform diameter of 280±5 µm. Each microsphere has about 0.0028 mg cyclosporine. An applicator with an extra thin-walled 27-g needle (i.d.=0.29 mm) can be filled with about 100 microspheres to reach a total drug content of about 0.27 mg. Total length of loaded microspheres in the needle is 28 mm, compared to 19 mm of a thermally extruded rod with a 280 µm diameter and 0.28 mg cyclosporine. The microspheres can be injected subconjunctivally and the drug is released over a period of three months.

Example 4

Microspheres are made with 80% polyanhydride (cpp:sa/80:20) and 20% Bimatoprost having a uniform diameter of 450±10 µm. Each microsphere has about 0.0163 mg Bimatoprost. An applicator with a thin-walled 22-g needle (i.d.=0.5 mm) can be filled with about 12 microspheres to reach a total drug content of about 0.2 mg. Total length of loaded microspheres in the needle is 5.4 mm, compared to 3.6 mm of a thermally extruded rod with a 450 µm diameter and 0.2 mg Bimatoprost. The microspheres can be injected subconjunctivally and the drug is released over a period of three months.

While this invention has been described with respect to various specific examples and embodiments, it is to be understood that the invention is not limited thereto and that it can be variously practiced within the scope of the following claims.

What is claimed is:

1. An apparatus (10) for implanting an ocular implant in an eye, the apparatus comprising:
   a) a housing (40);
   b) a cannula (12) having a lumen (14) extending therethrough, the lumen having a length and a diameter and comprising an ocular implant, said implant comprising a plurality of substantially uniformly sized and substantially spherical particles (18) in a one-by-one array along the length of the lumen, wherein the apparatus includes substantially no liquid material present in the lumen with the plurality of particles, such that the particles can be delivered into the eye in a dry state;
   c) a push rod (22) that is slidably receivable within the lumen and movable from a first position to a second position and that terminates at its proximal end in a cone (49);
   d) a cam (70) disposed within the housing, wherein the end of the cam is located proximal to the cone such that rotation of the cam causes the end of the cam to engage the cone, causing translation movement of the push rod relative to the cannula and ejection of the implant from the cannula;
   e) a movement assembly (28) operatively coupled to the push rod and structured to move the push rod from the first position to the second position, the cannula having a slight bend incorporated into the tip in order to hold the particles within the lumen before movement of the push rod to the second position;
   f) the movement assembly including a lever (54) for downward movement normal to the longitudinal axis of the apparatus, wherein downward movement of the lever causes rotational movement of the cam, one end of the lever terminating in a button (58), the other end terminating in a tab (60) engageable with a latch (62) on the housing, wherein when the lever is fully depressed and the implant ejected, the tab engages the latch thereby locking the assembly into a depressed, post-ejection, condition.

2. The apparatus of claim 1 wherein the diameter of the lumen is substantially uniform in size along the length of the lumen.

3. The apparatus of claim 1 wherein the diameter of the lumen is about 350 microns or less.

4. The apparatus of claim 1 wherein the lumen has a diameter in a range of about 200 microns to about 500 microns.

5. The apparatus of claim 1 wherein the lumen has a diameter in a range of about 250 microns to about 300 microns.

6. The apparatus of claim 1 wherein the maximum transverse dimension of each particle of the plurality of particles is at least about 70% of the diameter of the lumen.

7. The apparatus of claim 1 wherein the maximum transverse dimension of each particle of the plurality of particles is at least about 80% of the diameter of the lumen.

8. The apparatus of claim 1 wherein the maximum transverse dimension of each particle of the plurality of particles is at least about 90% of the diameter of the lumen.

9. The apparatus of claim 1 wherein the plurality of particles includes a smallest particle and a largest particle having a maximum transverse dimension within about 20% of the maximum transverse dimension of the smallest particle.

10. The apparatus of claim 1 wherein the plurality of particles includes a smallest particle and a largest particle having a maximum transverse dimension within about 10% of the maximum transverse dimension of the smallest particle.

11. The apparatus of claim 1 wherein the plurality of particles includes a smallest particle and a largest particle having a maximum transverse dimension within about 5% of the maximum transverse dimension of the smallest particle.

12. The apparatus of claim 1 wherein the plurality of particles includes a number of particles in a range of about 10 to about 200.

13. The apparatus of claim 1 wherein the plurality of particles includes a number of particles in a range of about 20 to about 75.

14. The apparatus of claim 1 wherein the plurality of particles includes particles having different compositions.

15. The apparatus of claim 1 wherein the cannula has an outside diameter no larger than a standard 22 gauge needle.

16. The apparatus of claim 1 wherein the cannula has an outside diameter equal to a 27 gauge needle.

17. The apparatus of claim 1 wherein the push rod and cannula are configured so that the push rod comes into physical contact with at least one particle of the plurality of particles in moving from the first position to the second position.

18. The apparatus of claim 1 wherein the push rod and cannula are configured so that the push rod comes into direct physical contact with only one particle of the plurality of particles in moving from the first position to the second position.

19. The apparatus of claim 1 wherein the plurality of particles comprise at least one therapeutic component effective to provide a therapeutic effect when released from the plurality of particles in an eye.

20. The apparatus of claim 19 wherein the plurality of particles further comprises a biodegradable polymer in combination with the at least one therapeutic component.

* * * * *